(12) United States Patent
Butler

(10) Patent No.: US 8,550,631 B2
(45) Date of Patent: Oct. 8, 2013

(54) GLARE ASSEMBLY FOR COMPUTERIZED EYE TEST DISPLAY

(75) Inventor: Kevin A. Butler, Downers Grove, IL (US)

(73) Assignee: M&S Technologies, Inc., Skokie, IL (US)

( * ) Notice: Subject to any disclaimer, the term of this patent is extended or adjusted under 35 U.S.C. 154(b) by 0 days.

(21) Appl. No.: 12/911,473

(22) Filed: Oct. 25, 2010

(65) Prior Publication Data

US 2011/0228228 A1    Sep. 22, 2011

Related U.S. Application Data

(60) Provisional application No. 61/254,410, filed on Oct. 23, 2009.

(51) Int. Cl.
*A61B 3/02* (2006.01)
*A61B 3/00* (2006.01)
*A61B 3/10* (2006.01)

(52) U.S. Cl.
USPC ............ 351/243; 351/200; 351/205; 351/221

(58) Field of Classification Search
USPC ......... 351/243, 239, 222, 246, 200, 203, 205, 351/221, 223, 224
See application file for complete search history.

(56) References Cited

U.S. PATENT DOCUMENTS

| | | | | |
|---|---|---|---|---|
| 4,800,404 A * | 1/1989 | Ginsburg et al. | ............. | 351/243 |
| 5,365,370 A * | 11/1994 | Hudgins | ....................... | 359/464 |
| 5,969,792 A * | 10/1999 | Ginsburg | ....................... | 351/243 |
| 6,783,239 B2 * | 8/2004 | Epitropoulos | ................ | 351/221 |
| 7,204,591 B2 * | 4/2007 | Wertheim et al. | ............. | 351/223 |

* cited by examiner

*Primary Examiner* — Dawayne A Pinkney
(74) *Attorney, Agent, or Firm* — Fay Sharpe LLP

(57) ABSTRACT

A monitor is used to display a visual acuity test operated by software from an associated computer. A patient is spaced a predetermined distance from the monitor during the testing procedure, and individual, multiple LED housings are equally spaced about a center point of the monitor to direct light toward the patient during at least a portion of the test procedure. The light emanating from the individual housings is a diffuse, unfocused light to simulate glare, and the intensity of the light may be selectively altered. Conducting acuity testing under glare conditions determines if there is any reduction or fall off in the patient's acuity vision under such circumstances and provides an indication of whether the patient may require cataract surgery or has another ocular problem.

9 Claims, 2 Drawing Sheets

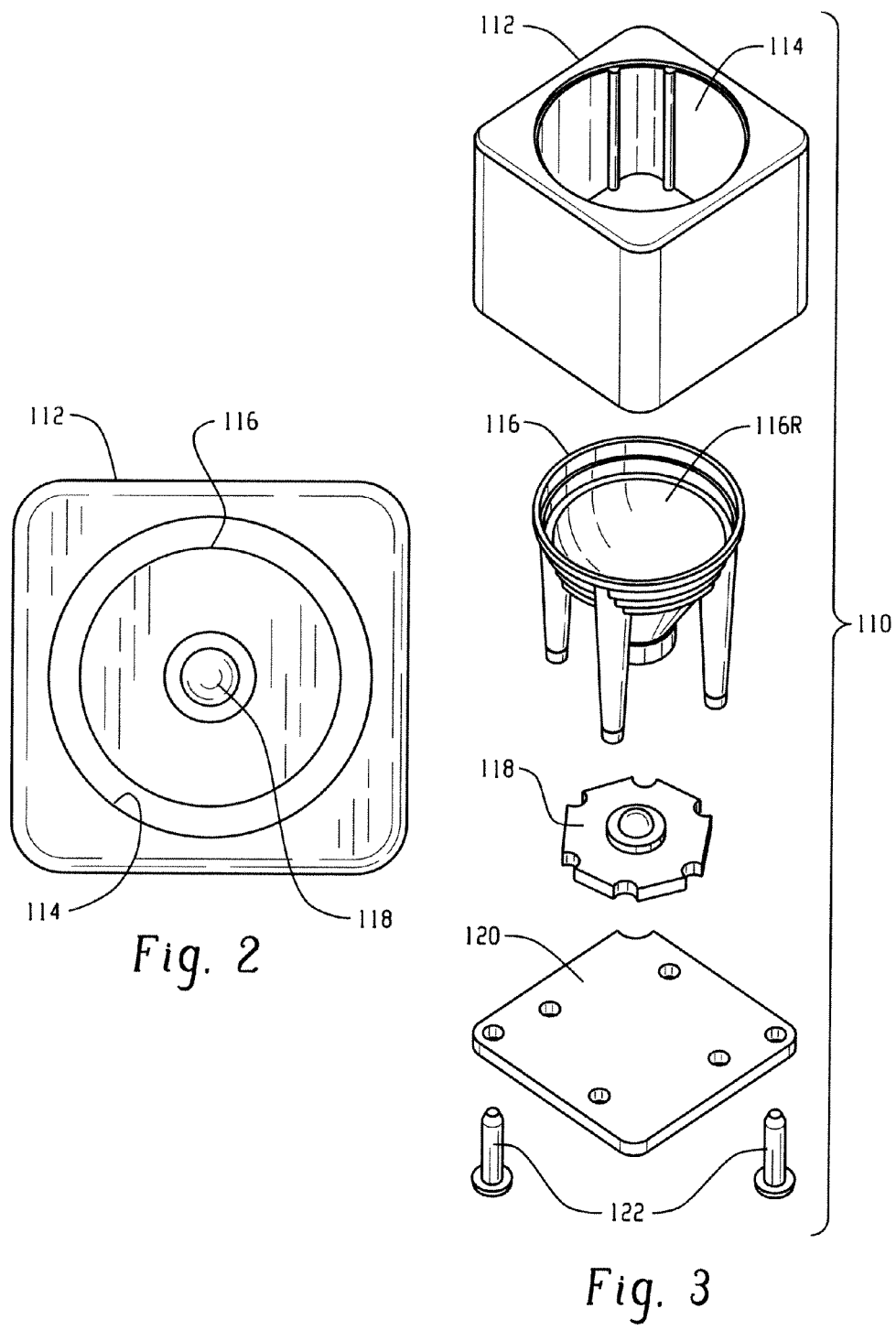

GLARE ASSEMBLY FOR COMPUTERIZED EYE TEST DISPLAY

This application claims priority from U.S. provisional application Ser. No. 61/254,410, filed 23 Oct. 2010, the disclosure of which is expressly incorporated herein in its entirety.

BACKGROUND OF THE DISCLOSURE

This disclosure relates to an eye test assembly, and more particularly to an eye test assembly that displays an eye chart on a computer monitor and the eye test is run by software. Further, the present disclosure relates to a glare assembly for use with such a display or monitor that is useful in diagnosing cataracts or other ocular problems or issues associated with a patient. Under normal testing conditions, a patient may demonstrate acceptable scores, for example even exhibiting 20/20 vision in an examination room under normal exam room conditions. Unfortunately, in the light of day, and in real world conditions, such as driving at night with on-coming headlights directed at the driver, or in bright sunlight, the patient's vision may be quite different due to bright light passing through the lens of the eye.

There are a couple of different products presently on the market that test for the impact of glare. For example, a Brightness Acuity Tester (BAT), as shown and described in U.S. Pat. No. 4,784,483. The disclosure of that patent is hereby incorporated by reference. An upright handle positions an open sided housing having an aperture or opening through the housing adjacent a patient's eye. A source of illumination is disposed in the housing and is varied between high, medium, and low settings. In this manner, a patient's vision is measured in a standard manner, and with one eye occluded, the brightness acuity tester is held adjacent the patient's eye under examination, the source of illumination turned on, and visual acuity of that eye is then measured with the patient looking through the glare light. In other words, glare light is purposefully introduced into the visual path of the patient. The comparison between these acuity testing procedures under non-glare and glare conditions will then determine whether the patient has any pronounced or recognizable change in acuity vision. This may be an indication of whether cataracts or other ocular problems exist.

Another type of commercially available device is one sold by Vector Vision. An illuminated eye chart box, or light box, for example the type as shown and described in U.S. Pat. No. 5,078,486, is modified to include first and second halogen lights secured on either side of the light box. The halogen lights are described as simulating an on-coming car with headlamps illuminated at a preselected distance. The halogen lights are either turned on or off. A particular line or row of characters on the light box is illuminated. An internal light source generates the desired light intensity on a particular row of the eye chart, and employs a sensor or photocell to monitor the light intensity in the ambient environment adjacent the eye chart. In this manner, the amount of light generated by the light source can be altered.

Although commercially successful, improvements are desired, particularly when used with a computer software visual acuity testing arrangement.

SUMMARY

A computer vision testing system includes a monitor for displaying a test procedure. Individual, multiple light sources equi-spaced about a center point of the monitor and directed toward an associated patient to conduct the test procedure under glare light conditions.

A method of testing visual acuity of a patient includes locating a monitor a predetermined distance from an associated patient, running a visual acuity test, displaying the test on the monitor, and directing light from individual light sources equi-spaced from a center point of the monitor toward the associated patient.

BRIEF DESCRIPTION OF THE DRAWINGS

FIG. 2 is a plan view of one of the LED light sources.

FIG. 3 is an exploded perspective view of one of the LED assemblies.

DETAILED DESCRIPTION OF THE PREFERRED EMBODIMENT

Figure 1:
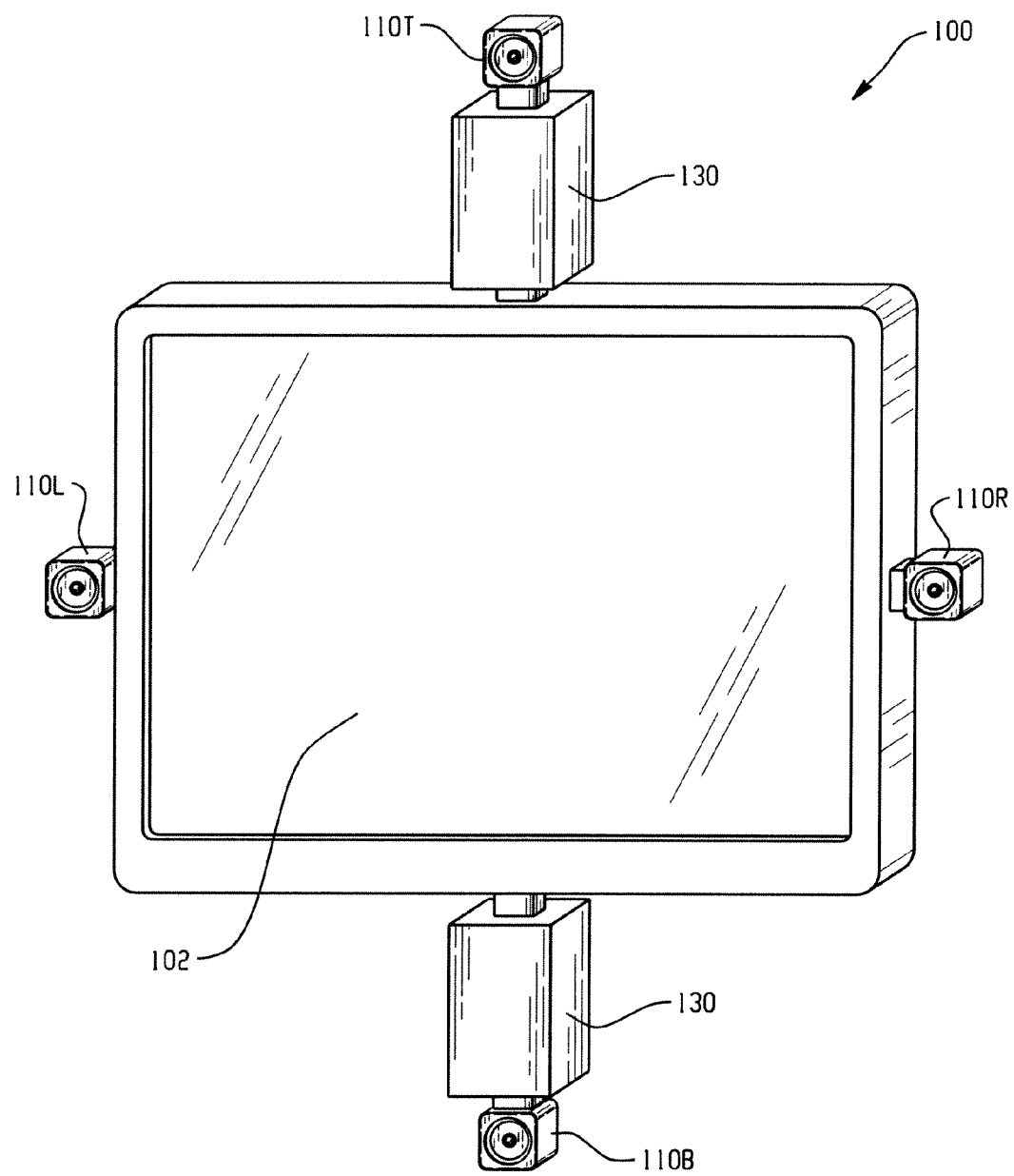
FIG. 1 is an elevational view of a computer monitor used as a display for conducting visual acuity testing.

Turning first to FIG. 1, there is a shown a monitor 100 used to display a visual acuity test operated by software from an associated computer (not shown), for example, of the type as shown and described in U.S. Published Application No. 20040036840A1. The illustrated monitor is rectangular, for example having a 16×9 rectangular aspect ratio. Although the illustrated monitor is of a liquid crystal display (LCD) type, it is also contemplated that a cathode ray tube (CRT) monitor could be employed without departing from the scope and intent of the present disclosure. Display face 102 is controlled by the visual acuity testing software. The testing usually occurs in a dark room in order to provide greater control over the luminance associated with the monitor and thus a more standardized testing. A patient is spaced a predetermined distance from the monitor during the testing procedure, and the size of the characters on the screen are controlled and calibrated. Preferably, multiple LEDs 110 are displayed around the monitor. Each LED 110 is of substantially identical structure as shown in FIGS. 2 and 3. For example, housing 112 includes an opening 114 along one surface of the generally cubical-shaped housing, although other housing conformations may be adopted without departing from the scope and intent of the present disclosure. The hollow housing receives a fraen lens and holder 116 that serves to direct light emitted from the LED through an opening 114 in the housing. For example, an inner reflective surface 116R reflects and directs light outward through the housing opening and toward the patient (not shown) who is typically seated a predetermined distance from the monitor. An LED light source 118 is mounted at one end of the holder 116 in order to direct light therethrough and ultimately through the opening 114 of the housing. A heat sink 120 is advantageously located on a rear surface of the light source in order to convey heat away from the elevated temperatures associated with operation of the LED. One or more fasteners, such as threaded screws 122 extend through the heat sink and into the LED housing in order to contain the light source in operative engagement with the lens and holder within the LED housing.

Each housing assembly 110 is then mounted to the perimeter of the monitor 100. Each LED housing disposed on a side portion of the monitor, i.e., on the right-hand and left-hand sides of the monitor are preferably disposed closely adjacent the perimeter of the monitor. As will be appreciated, in this manner, and with the display face centered within the perimeter of the monitor, the housing assemblies 110 are equi-spaced from a left-to-right center portion of the display face, and preferably at equal distances from the center. For ease of reference, these housing assemblies are referred to as 110L and 110R. Further, additional LED housing assemblies 110T, 110B are provided on extensions 130 that space the top and bottom LED housing assemblies from the upper and lower perimeters, respectively, of the monitor. Each of the housing assemblies is centered left-to-right, and preferably equi-spaced top-to-bottom away from a central point in a monitor, i.e., by the same distance as each of the LED housing assemblies 110L, 110R. In this manner, each LED housing is equally spaced from the center point of the monitor.

Using four perimeter spaced light sources is also preferred to simulate a circle of light. In some instances, a pair of light sources (either positioned on either side or spaced top to bottom) may be insufficient. Further, the light emanating from the individual housings is a diffuse light, i.e., not focused light. Ultimately, a diffuse light source that is provided in a relatively even manner from the periphery of the screen to simulate glare is desirable for glare testing. Conducting acuity testing under glare conditions to determine if there is any reduction or fall off in the patient's acuity vision under such circumstances provides an indication, for example, of whether the patient may require cataract surgery or has another ocular problem.

Each LED housing assembly connects to the computer assembly, preferably through a USB port or the like, and in the presently preferred arrangement communicates with the processor through a serial-type protocol. The processor controls not only an on/off condition of the LEDs, but also allows the brightness of each to be adjusted between one of approximately two-hundred ten (210) levels of brightness. The intensity of the three watt LEDs supplied by a twenty four (24) volt power supply will vary depending on the distance from the patient. Since the distance of the patient from the monitor can be inputted to the software, the software can then compute a desired intensity level of brightness based on this measurement distance. Thus, although there are generally three general levels (high, medium and low which are dependent on the measurement distance of the patient from the light source), the levels of glare light intensity can be further manipulated with the teachings of the present disclosure if so desired. The patient can be tested in a variety of ambient light conditions because the glare lights can be adjusted.

Preferably, each of the LED housing assemblies that serve to provide glare light provides a diffuse light source that faces the patient. Particularly, with two, and preferably four or more LED housing assemblies, a more uniform diffused glare light is directed toward the patient while the visual acuity testing is undertaken under the glare light condition.

The invention has been described with reference to the preferred embodiments. Modifications and alterations will occur to others upon reading and understanding this specification. It is intended to include all such modifications and alterations in so far as they come within the scope of the appended claims or the equivalents thereof.

What is claimed is:

1. A computer vision testing system comprising:
a monitor for displaying a visual acuity test procedure; and
at least first, second, third and fourth diffuse, unfocused light sources equi-spaced about a center point of the monitor and directed toward an associated patient to conduct the test procedure displayed on the monitor under glare light conditions, wherein the first and second light sources are disposed above and below the monitor, and the third and fourth light sources are disposed along first and second sides of the monitor wherein the light sources each simultaneously emit diffuse, unfocused light for both eyes.

2. The system of claim 1 wherein the intensity of the light sources may be selectively altered.

3. The system of claim 2 wherein the desired intensity of the light sources is based on a dimension that an associated patient is spaced from the monitor.

4. The system of claim 1 wherein each of the light sources is identical to the other light sources.

5. The system of claim 1 wherein each of the light sources is a light emitting diode (LED).

6. A method of testing visual acuity of a patient comprising:
locating a monitor a predetermined distance from an associated patient;
running a visual acuity test;
displaying the test on the monitor;
directing diffuse, unfocused light simultaneously from at least first, second, third and fourth individual light sources equi-spaced from a center point of the monitor toward both eyes of the associated patient; and
locating the first and second light sources above and below the monitor, respectively, and locating the third and fourth light sources along first and second sides of the monitor, respectively.

7. The method of claim 6 further comprising selectively altering an intensity of the light sources.

8. The method of dam 6 further comprising selectively altering an intensity of the light sources.

9. A computer vision testing system comprising:
a monitor for displaying a visual acuity test procedure; and
at least first, second, third and fourth diffuse, unfocused light sources equi-spaced about a center point of the monitor and directed toward an associated patient to conduct the test procedure displayed on the monitor under glare light conditions, wherein the first and second ht sources are disposed above and below the monitor, and the third and fourth light sources are disposed along first and second sides of the monitor wherein the light sources each simultaneously emit diffuse, unfocused light for both eyes.

* * * * *